United States Patent [19]

Bohlmann et al.

[11] Patent Number: 4,925,834
[45] Date of Patent: May 15, 1990

[54] 3-METHYLENE-4-ANDROSTEN-17-ONES, PROCESS FOR THEIR PRODUCTION AND PHARMACEUTICAL PREPARATIONS CONTAINING THEM

[75] Inventors: Rolf Bohlmann; Henry Laurent; David Henderson; Yukishige Nishino, all of Berlin, Fed. Rep. of Germany

[73] Assignee: Schering Aktiengesellschaft, Berlin and Bergkamen, Fed. Rep. of Germany

[21] Appl. No.: 188,569

[22] Filed: Apr. 29, 1988

[30] Foreign Application Priority Data

Apr. 30, 1987 [DE] Fed. Rep. of Germany ....... 3714965

[51] Int. Cl.$^5$ .......................... A61K 31/56; C07J 1/00
[52] U.S. Cl. .................... 514/177; 514/178; 552/526; 552/632; 552/636; 552/615; 540/114
[58] Field of Search ............................. 514/177, 178; 260/397.3, 397.4

[56] References Cited

U.S. PATENT DOCUMENTS

| | | | |
|---|---|---|---|
| 3,239,419 | 3/1966 | Bruckner et al. | 260/397.3 |
| 3,301,880 | 1/1967 | van Vliet et al. | 260/397.3 |
| 3,450,720 | 6/1969 | La Lancette | 260/397.3 |
| 4,289,762 | 9/1981 | Metcalf et al. | |
| 4,473,564 | 9/1984 | de Winter | 514/170 |
| 4,546,098 | 10/1985 | Fishman et al. | 514/177 |

FOREIGN PATENT DOCUMENTS

| | | | |
|---|---|---|---|
| 161492 | 11/1985 | European Pat. Off. | |
| 1451985 | 10/1964 | France | 260/397.3 |

OTHER PUBLICATIONS

Brodie, A. M., et al., "Studies on the Mechanism of Estrogen Biosynthesis in the Rat Ovary," *J. Steroid Biochem.*, 1976, vol. 7, pp. 787–791.
*Chemical Abstracts*, vol. 105, Nr. 9, 1, Sep. 1, 1986.

Primary Examiner—Joseph A. Lipovsky
Attorney, Agent, or Firm—Millen, White & Zelano

[57] ABSTRACT

A 3-methylene-4-androsten-17-one of formula I

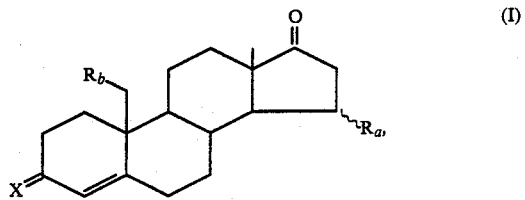

wherein $R_a$ represents a hydrogen atom or a saturated or unsaturated straight-chain or branched-chain, optionally substituted alkyl radical with 1–6 carbon atoms, in which $R_a$ is in the alpha- or beta-position, and $R_b$ represents a hydrogen atom, a hydroxyl or an —S-(O)$_n$R$_c$ group, in which R$_c$ is a hydrogen atom or an alkyl or acyl group with 1–4 carbon atoms, n=0, 1 or 2, and X represents CH$_2$, CHF, CHCl or CHBr, in which if $R_a$ is hydrogen and $R_b$ is hydroxyl or $R_a$ and $R_b$ each are hydrogen, X is not CH$_2$.

The new compounds of formula I are suitable for fertility control and for treatment of diseases which are promoted by estrogens.

17 Claims, No Drawings

3-METHYLENE-4-ANDROSTEN-17-ONES, PROCESS FOR THEIR PRODUCTION AND PHARMACEUTICAL PREPARATIONS CONTAINING THEM

BACKGROUND OF THE INVENTION

The invention relates to 3-methylene-4-androsten-17-ones, process for their production and pharmaceutical preparations containing them. The invention also relates to the use of these compounds as inhibitors of estrogen biosynthesis.

Thus, the invention also relates to pharmaceutical preparations and the use of the new compounds of formula I for the production of these preparations for treatment of diseases affected by estrogen.

SUMMARY OF THE INVENTION

It is an object of the invention to provide improved estrogen biosynthesis inhibitors, having pharmaceutical utility.

Upon further study of the specification and appended claims, further objects and advantages of this invention will become apparent to those skilled in the art.

These objects have been satisfied by the provision of compounds of the formula I:

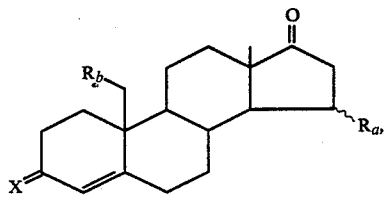

wherein $R_a$ represents a hydrogen atom or a saturated or unsaturated, e.g. alkyl or alkenyl, straight-chain or branched-chain radical with 1-6 carbon atoms, in which $R_a$ is in the alpha- or beta-position, or such an alkyl or alkenyl radical substituted, e.g., by hydroxy, halo (chloro, brono, floro, iodo), $C_1$-alkanoyl, bis hydroxy or bis $C_{1-4}$-alkanyol and $R_b$ represents a hydrogen atom, a hydroxyl group or an $-S(O)_nR_c$ group, in which $R_c$ is a hydrogen atom or an alkyl or acyl, e.g., alkanoyl, group with 1-4 carbon atoms, n=0, 1 or 2, and X represents $CH_2$, CHF, CHCl or CHBr, in which X is not $CH_2$ is $R_a$ represents hydrogen and $R_b$ represents hydroxyl, or if $R_a$ and $R_b$ are each hydrogen.

The alkyl or alkenyl groups $R_a$ are to be straight-chain or branched-chain, substituted or unsubstituted and contain 1-6 carbon atoms. These alkyl groups can be in the alpha- or beta-position on the steroid skeleton. Preferably they are the methyl, ethyl, propyl, butyl, hexyl, 2-methylpropyl, 3-methylbutyl, ethenyl, hydroxymethyl, 2-chloroethyl, 1-acetoxyethyl and 1,2-bis-(acetoxy)butyl groups, as well as all isomers and stereoisomers of these groups.

The groups standing for $R_b$ can be a hydrogen atom, a hydroxyl or an $-S(O)_{nn}R_c$ group, in which n=0, 1 or 2 and $R_c$ represents a hydrogen atom or an alkyl or acyl group with 1-4 carbon atoms, for example, such as where $R_b$ is a methylthio, ethylthio, propylsulfinyl, butylsulfonyl or an acetylthio group. The sulfur functionality in the 19 position can be present as a thioether, sulfoxide, sulfone or thioacylate.

The compounds according to the invention of the formula

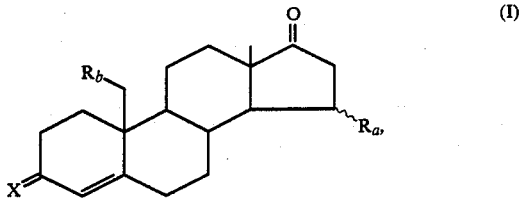

wherein $R_a$ represent a hydrogen atom or a straight-chain or branched-chain, optionally substituted alkyl or alkenyl radical with 1-6 carbon atoms, in which $R_a$ is in the alpha- or beta-position, and $R_b$ represents a hydrogen atom, a hydroxyl or an $-S(O)_nR_c$ group, in which $R_c$ is a hydrogen atom or an alkyl or acyl group with 1-4 carbon atoms, n=0, 1 or 2, and X represents $CH_2$, CHF, CHCl or CHBr, in which X is not $CH_2$, if $R_a$ represents hydrogen and $R_b$ represents hydroxyl or $R_a$ and $R_b$ represent hydrogen in each case, can be produced from a compound of formula II

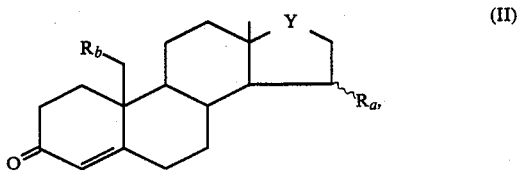

wherein $R_a$ represents a hydrogen atom or a straight-chain or branched-chain, optionally substituted alkyl or alkenyl radical with 1-6 carbon atoms, in which $R_a$ is in the alpha- or beta-position, and $R_b$ represents a hydrogen atom, a hydroxyl or an $-S(O)_nR_c$ group, in which $R_c$ is a hydrogen atom or an alkyl or cyl group with 1-4 carbon atoms, and n=0, 1 or 2, and Y represents a carbonyl or hydroxymethylene group. This compound (II) is reacted with a phosphorylide of formula III $$(R_d)_3P=X \qquad (III)$$

wherein

X represents $CH_2$, CHF, CHCl or CHBr, in which X is not $CH_2$, if $R_a$ represents hydrogen and $R_b$ represents hydroxyl or if $R_a$ and $R_b$ both represent hydrogen, and $R_d$ represents a saturated or unsaturated or aromatic hydrocarbon radical with 1-10 carbon atoms. The resultant product may optionally be oxidized, for example, where Y is a hydroxymethylene group.

The production of the compounds of formula I takes place by means of reactions which are known to one of ordinary skill in the art (see, for example, Pure Appl. Chem. 1980, 52, 771; Top. Stereochem, 1970, 5, 1; A. W. Johnson, "Ylid-Chemistry" in Academic Press (1966) and European patent application publication No. 161,492). The triphenylphosphonium floromethylene Wittig reagent is produced as described in J. Fluorine Chem. 1985, 27, 85. Similar chlorine and bromine derivatives are available on the market.

Oxidation of the compounds of formula II to compounds of formula I is optionally performed according to Oppenauer (Org. React. 1951, 6, 207). Further, it is possible to oxidize a thioether or a sulfoxide in the radical $R_b$ of formula II with known methods to produce the sulfoxide and sulfone or to the sulfone.

Methods for oxidation known from the literature include reactions with hydrogen peroxide, organic peracids, e.g., chloroperbenzoic acid, and inorganic peroxides, e.g., nickel or molybdenum peroxide [Arch. Pharm. (Weinheim), 316, 941, 1983 ].

The compounds of formula I are inhibitors of estrogen biosynthesis (aromatase i hibitors). Thus they are suitable for treatment of diseases which are caused by estrogens or are dependent on estrogens. Thus, they are suitable for treatment of estrogen-induced or estrogen-stimulated tumors, as, for example, mastocarcinoma or benign prostatic hyperplasia (The Lancet, 1984, 1237-1239).

The compounds according to the invention are also valuable for influencing fertility. Thus, male infertility, which results from increased estrogen levels, can be overcome with the new active compounds.

Further, the compounds can be used with women of reproductive age as an antifertility agent to inhibit ovulation or implantation by estrogen deprivation.

Aromatase inhibitors are also suitable for treatment of impending myocardial infarction, since increased estrogen levels can precede a myocaridal infarction in the male (U.S. Pat. No. 4,289,762).

Known steroid substances enhibiting action inhibiting aromatase are, for example, 4-hydroxyandrost-4-ene-3,17-dione and its ester (see, for example, U.S. Pat. No. 4,235,983) and 3-methylene-4-androsten-17 -one (European patent application No. 161,492).

In comparison with known aromatase inhibitors serum estradiol concentration is greatly reduced with the compounds according to the invention in oral application. The following test shows the effectiveness of the compounds according to the invention.

Infantile female rats react to PMSG (Pregnant Mare's Serum Gonadotropin) treatment with uniformly increased steroid synthesis. The aromatase activity can be measured by the influence of the estrogen formation stimulated by PMSG. [J. Steroid. Biochem., 7 (1976) 787] Anit-tumor activity in humans of compounds which have a positive effect in the PMSG test is described in The Lancet, 1 Dec. 1984, ppg. 1237-1239.

In the so-called PMSG test 21-day-old female rats are pretreated subcutaneously every other day for a total of 7 times with 100 IU of PMSG each time. 1 hour before and 8 hours after the last PMSG application ($d_{12}$) the animals receive the test substance by oral dose. They are killed 24 hours after the last PMSG application. The estradiol is examined radioimmunologically in the serum. The average value of the estradiol concentration in nmol/l with standard deviation is calculated for each group of 10 animals. The significance of the differences from the control group are examined by analysis of variance.

The percentage inhibition is calculated against the PMSG control.

The aromatase inhibitors 4-hydroxy-4-androstene-3,17-dione (A) and 3-methylene-4-androsten-17-one (B), known from the literature, exhibit no effectiveness in oral application in the test does range (2×10 mg). On the other hand, the compound according to the invention 3-fluoromethylene-19-methylthio-4-androsten-17-one (C) exhibits a markd inhibition effectiveness in the test with 45% inhibition.

TABLE

| PMSG Test in Infantile Rats, Orally | | |
|---|---|---|
| Dose | Concentration in Serum | |
| mg/animal 2 × p.o. | estradiol nmol/l | % inhibition |
| PMSG controls — | 6.21 ± 1.78 | — |
| A 10 | 6.08 ± 0.56 | 0 |
| B 10 | 6.20 ± 0.80 | 0 |
| C 10 | 3.24 ± 0.81 | 45 |

The amount of the compound to be administered flucturates within a wide range and can cover any effective amount. Depending on the condition to be treated and the type of administration the amount of the administered compound can be 0.01–100 mg/kg of body weight, preferably 0.01–20 mg/kg of body weight per day. The dosage is 0.001–100 mg/kg/day, preferably 0.001–20 mg/kg/day, analogous to the known agent aminoglutethimide when administered to treat estrogen-stimulated tumors, 0.001–100 mg/kg/day, preferably 0.01–20 mg/kg/day when administered analogous to the known agent aminoglutethimide to treat male infertility, 0.001–100 mg/kg/day, preferably 0.1–20 mg/kg/day when administered analogously to the known agent 4-hydroxy-4-androstene-3,17 -dione to inhibit ovulation, and 0.02–30 mg/kg/day, preferably 0.1–20 mg/kg/day when administered analogously to the known agent 4-hydroxy-4-andorstene-3, 17-dione for the treatment of imminent myocardial infarction.

Capsules, pills, tablets, dragess, etc., are suitable for oral administration. Besides the active ingredient, the dosage units can contain a pharmaceutically compatible vehicle such as, for example, starch, sugar, sorbitol, gelatin, lubricant, silicic acid, talc, etc. The individual dosage units for oral application can, for example, contain 10–100 mg of the active ingredient (aromatase inhibitor).

For parennteral administration the active ingredient can be dissolved or suspended in a physiologically well tolerated diluent. Very often oils with or without addition of a solubilizer, of a surfactant, of a suspending agent or an emulsifying agent are used as diluents. Oils used are, for example, olive oil, peanut oil, cottonseed oil, soybean oil, castor oil and sesame oil.

The compounds can also be used in the form of a depot injection or an implant preparation, which can be formulated so that a delayed active ingredient release is made possible.

Implants can contain as inert materials, for example, biodegradable polymers or synthetic silicons, as, for example, silicone rubber. The active ingredients can further be incorporated for a percutaneous application, for example, in a plaster.

Without further elaboration, it is believed that one skilled in the art can, using the preceding description; utilize the present invention to its fullest extent. The following preferred specific embodimwents are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire text of all applications, patents and publications, if any, cited above and below are hereby incorporated by reference.

Production of the initial compounds (1) 15-alpha-ethyl-19-hydroxy-4-androstene-3,17-dione (a) 50.3 g of 3-beta-hydroxy-5,15-androstadien-17-one [R. W. Kelly and P. J. Sykes, J. Chem. Soc. (C), 416 (1968)] is mixed in 1.06 l of tetrahydrofuran with 60.8 g of potassium cynaide in 350 ml of water and refluxed for 15 minutes. Then it is diluted with water and extracted twice with ethyl acetate. 53 g of 15-beta-cyano-3-beta-hydroxy-5-androsten-17-one is obtained as raw product.

(b) 22.8 g of 15-beta-cyano-3-beat-hydroxy-5-androsten-17-one is mixed in 600 ml of methanol and 300 ml of tetrahydrofuran with 11.5 g of sodium borohydride and 46 ml of water in portions and stirred for 15 minutes at 20° C. Then it is poured into 10 l of ice water, the precipitate is suctioned off, washed neutral with water and dried in a drying cabinet at 70° C. overnight. The raw product is crystallized from acetone/toluene (1:1). 20.6 g of 15-beta-cyano-5-androstene-3-beta,17-beta-diol with a melting point of 251°–255° C. is obtained.

(c) 18.6 g of 15-beta-cyano-5-androstene-3-beta,17-beta-diol is refluxed in 700 ml of tetrahydrofuran under argon with 36 g of potassium tert-butylate in 300 ml of tetrahydrofuran for 15 minutes. The reaction point crystallizes out upon cooling. 16.4 of 15-alpha-cyano-5-androstene-3-beta,17-beta-diol is obtained by suctioning off te crystals.

(d) 5 g of 15-alpha-cyano-5-androstene-3-beta,17-beta-diol is mixed drop by drop in 200 ml of tetrahydrofuran at −15° C. with 150 ml of diisobutyl aluminum hydrode solution (1.0M in tetrahydrofuran) and stirred for 2 more hours at 0° C. Then 300 ml of 10% aqueous tartaric acid is added by portions, dropped into 400 ml of water and 200 g of ice, suctioned of, washed with water and drid. After crystallization from acetone 4.0 g of 3-beta,17-beta-dihydroxy-5-androstene-15-alpha-carbaldehyde with a melting point of 171°–173° C. (decomposition) is obtained.

(e) 19.7 g of 3-beta,17-beta-dihydroxy-5-androstene-15-alpha-carbaldehyde is added at 20° C. to a mixture of 56 g of triphenylmethyl phosphonium bromide in 490 ml of dimethyl sulfoxide and 17.6 g of potassium tert-butylate and stirred for 2 hours at 20° C. It is then precipitated with dilute sulfuric acid and extracted twice with ethyl acetate. The combined organic phase is washed with water and sodium chloride solution, dried on sodium sulfate and concentrated in a vacuum. The resulting product is stirred in 500 ml of 0.2N methanolic potassium hydroxide solution for 3.5 hours at 20° C. Then it is neutralized with ethyl acetate, precipitated with ice water, washed with water and concentrated in a vacuum at 70° C. 32 g of raw 15-alpha-vinyl-5-androstene-3-beta,17-beta-diol is obtained which is contaminated with triphenylphosphine.

(f) 32 g of 15-alpha-vinyl-5-androstene-3-beta,17-beta-diol is shaken in 450 ml of methanol with 3.2 g of palladium (;n 10%) on activated carbon for 1.5 hours under hydrogen. The catalysts is filtered off over silica gel, rewashed with dichloromethane and the organic phase is concentrated in a vacuum. 32 g of raw 15-alpha-ethyl-5-androstene-3-beta,17-beta-diol is obtained.

(g) 3.9 g of 15-alpha-ethyl-5-androstene-3-beta,17-beta-diol is stirred i 50 ml of pyridine with 25 ml of acetic anhydride for 17 hours at 20° C. Then it is precipitated with hydrochloric acid brine/ice water, filtered off, washed with water, taken up with dichloromethane, washed neutral, dried on sodium sulfate and concentrated. 4.1 g of 3,17-diacetoxy-15-alpha-ethyl-5-androstene is obtained after chromatographic purification on silica gel with hexane/ethyl acetate.

(h) 4.1 g of 3-beta,17-beta-diacetoxy-15-alpha-ethyl,5-androstene in 62 ml of diethyl ether is mixed at 0° C. with 3.1 g of N-bromosuccinimide and with a solution of 18 ml of 70% perchloric acid and 44 ml of water and stirred 0.5 hour. Then it is mixed with sodium sulfatesolution, extracted with ethyl acetate, washed neutral, dried on sodium sulfate and concentrated in a vacuum. 5.0 of raw 3-beta,17-beta-diacetoxy-5-alpha-bromo-15-alpha-ethyl-6-beta-androstanol is obtained.

(i) 5.0 g of 3-beta,17-beta-diacetoxy-5-alpha-bromo-15-alpha-ethyl-6-beta-androstanol in 175 ml of cyclohexane is refluxed with 2.5 g of lead tetraacetate and 1.6 g of iodine for 2.5 hours. Then the solid is filtered off, washed with ethyl acetate, the filtrate is washed with sodium thiosulfate, water and sodium chloride solution, dried on sodium sulfate and concentrated in a vacuum. 4.8 g of raw 3-beta,17-beta-diacetoxy-5-alpha-bromo-15-alpha-ethyl-5-beta,19-oxidoandrostane is obtained.

(j) 4.8 g of raw 3-beta,17-beta-diacetoxy-5-alpha-bromo-15-alpha-ethyl-6-beta,19-oxidoandrostane in 80 ml of glacial acetic acid is stirred with 9.6 g of zinc for 3 hours at 20° C. Then the zinc is filtered off by suction, washed with ethyl acetate, washed neutral with sodium hydrogen carbonate and sodium chloride solution, dried on sodium sulfate and concentrated. After chromatographic purification on silica gel with hexane/ethyl acetate, 950 g of pure 3-beta,17beta-diacetoxy-15-alpha-ethyl-19-hydroxy-5-androstene is obtained as a foam.

(k) 6.24 g of 3-beta,17beta-diacetoxy-15-alpha-ethyl-19-hydroxy-5-androstene in 62 ml of tetrahydrofuran is stirred with 6.24 ml of dihydropyran and 31.2 mg of p-toluenesulfonic acid for 1.5 hours at 20° C. Then 1 ml of pyridine is added, diluted with ethyl acetate, washed with sodium hydrogen carbonate and sodium chloride solution, dried on sodium sulfate and concentrated in a vacuum. After chromatographic purification on silica gel with hexane/ethyl acetate, 5.1 g of pure 3-beta,17-beta-diacetoxy-15-alpha-ethyl-19-(tetrahydropyran-2-yloxy)-5-androstene is obtained as foam.

(l) 5g of 3-beta,17-beta-diacetoxy-15-alpha-ethyl-19-(tetrahydropyran-2-yloxy)-5-androstene is stirred with 200 ml of a 0.2N methanolic potassium hydroxide solution for 3 hours at 20° C. Then it is neutralized with 10% acetic acid solution, the solution is concentrated to one-third, precipitated in ice water/common salt, filtered off, washed, taken up in dichloromethane, washed neutral, dried on sodium sulfate and concentrated. 3.94 g of 15-alpha-ethyl-19-(tetrahydropyran-2-yloxy)-5-androstene-3-beta,17-beta-diol with a melting point of 163°–164° C. is obtained.

(m) 3.54 g of 15-alpha-ethyl-19-(tetrahydropyran-2-yloxy)-5-androstene-3-beta,17-beta-diol is suspended in 285 ml of toluene and boiled with 106 ml of cyclohexanone and 3.54 g of aluminum triisopropylate for 5 hours on a water separator. Then it is concentrated in a vacuum, potassium sodium tartrate solution added, distilled for 1 hour with steam, extracted three times with dichloromethane, washed neutral, dried on sodium sulfate and concentrated in vacuum to dryness. After chromatograpy, 2.69 g of 15-alpha-ethyl-19-(tetrahydropyran-2-yloxy)-4-androstene-3,17-dione is obtained as foam.

(n) 2.64 g of 15-alpha-ethyl-19-(tetrahydropyran-2-yloxy)-4-androstene-3,17-dione in 66 ml of acetone is stirred with 3.3 ml of half-concentrated hydrochloric acid for 5.5 hours at 20° C. Then it is neutralized with saturated sodium hydrogen carbonate solution, diluted with water, extracted three times with dichloromethane, washed neutral, dried on sodium sulfate and concentrated in a vacuum. 2.652 g of raw product is obtained and after chromatographic purification on silica gel with dichloromethane/acetone 1 g of pure 15-alpha-ethyl-19-hydroxy-4-androstene-3,17-dione with a melting point of 123°-125° C. is obtained.

(2) 151 -beta-ethyl-19-hydroxy-4-androstene-3,17-dione 50 g raw 15-beta-cyano-3-beta-hydroxy-5-androsten-17-one is stirred in 950 ml of tetrahydrofuran at −20° C. with 950 ml of diisobutyl aluminum hydride solution (1.2M in toluene) for 2.5 hours. Then it is mixed with dilute sulfuric acid, suctioned off over kieselguhr, the organic phase is washed neutral with sodium hydrogen carbonate solution, dried on sodium sulfate and concentrated in a vacuum. 50.1 g of raw 3-beta,17-beta-dihydroxy-5-androstene-15-beta-carbaldehyde is obtained.

The further processing to 15-beta-ethyl-19-hydroxy-4-androstene-3,17-dione takes place similarly to the processing of the initial compounds 1 e)–n).

EXAMPLE 1

3-Chloromethylene-19-methylthio-4-androsten-17-one 500 mg of 19-methylthio-4-androstene-3,17-dione (European patent 100,566) is added to a suspension of 5.21 g of chloromethyl triphenylphosphonium chloride in 50 ml of tetrahydrofuran, which was stirred with 9.5 ml of (1.6 m of butyllithium in ether) 0.5 hours at 20° C., and stirred for 30 minutes at 0° C. Then it is mixed with water, extracted three times with ethyl acetate, washed neutral, dried on sodium sulfate and concentrated to dryness. 995 mg of raw product is obtained, which after chromatographic purification yields 273 mg of pure 3-chloromethylene-19-methylthio-4-androsten-17-one with a melting point of 114°-115° C., $[\alpha]_D +241.5°$ C. (CHCl$_3$), as pure E form.

EXAMPLE 2

3-Fluoromethylene-19-methylthio-4-androsten-17-one 500 ml of 19-methylthio-4-androsten-3,17-dione (Euoprean patent 100,566) in 10 ml of dimethoxyethane is added drop by drop at 0° C. to a suspension of 5.73 g of fluoromethyl triphenylphosphonium tetrafluoroborate in 40 ml of dimethoxyethane, which was stirred with 9.5 ml of butyllithium solution (1.6 m in ether) for 0.5 hour, instilled and stirred for another 15 minutes. Then saturated ammonium chloride solution is added, diluted with water, extracted three times with ethyl acetate, washed neutral, dried on sodium sulfate and concentrated in a vacuum. After chromatography on silica gel with hexane/ethyl acetate, 331 mg of pure 3-fluoromethylene-19-methylthio-4-androsten-17-one with a melting point of 146°-147° C. $[\alpha]_D +288.4°$ (CHCl$_3$) as E:Z mixture is obtained.

EXAMPLE 3

15-alpha-ethyl-3-methylene-19-hydroxy-4-androsten-17-one 2.7 g of 15-alpha-ethyl-19-hydroxy-4-androstene-3,17-dione in 25 ml of tetrahydrofuran is instilled in a suspension of 28.6 of methyl triphenylphosphonium bromide in 200 ml of tetrahydrofuran, which was stirred with 200 ml of butyllithium solution (1.6 m in ether) for 1.5 hours at 20° C., and stirred for one hour at 20° C. Then it is mixed with water, extracted three times with ethyl acetate, washed neutral, dried on sodium sulfate and is freed from the solvent in a vacuum. After chromatographic purification on silica gel with hexane/ethyl acetate, 1.95 g of pure 15-alpha-ethyl-3-methylene-19-hydroxy-4-androsten-17-one is obtained as foam.

UV: $\epsilon_{239} = 13670$.

EXAMPLE 4

15-beta-ethyl-3-methylene-19-hydroxy-4-androsten-17-one

The production takes place by reaction of 15-beta-ethyl-19-hydroxy-4-androsten-3,17-dione with methyl triphenylphosphonium bromide similarly to example 3. 15-beta-ethyl-3-methylene-19-hydroxy-4-androsten-17-one is obtained as foam.

UV: $\epsilon_{239} = 13700$.

EXAMPLE 5

3-Fluoromethylene-4-androsten-17-beta-ol 17.2 g of fluoromethyl triphenylphsophonium tetrafluoroborate is suspended in 150 ml of dioxane and mixed at 25° C. in portions with 6.74 g of potassium tert-butylate. Stirring is continued for another half hour at 25° C., 3 g of testosterone is added and stirring is continued for another 10 minutes at 25° C. Then the reaction mixture is added to water, extracted three times with dichloromethane, the organic phases are washed neutral, dried on sodium sulfate and freed from the solvent in a vacuum. After chromatography on silica gel with hexane/ethyl acetate, 623 mg of (E)-3-fluoromethylene-4-androsten-17-beta-ol with a melting point of 138°-140° C., X$_1$, besides 1.24 g of (Z)-3-fluoromethylene-4-androstene-17-beta-ol with a melting point of 125°-126° C., X$_2$.

$X_1 + [\alpha]_D + 148.4°$ (CHCl$_3$), $X_2 = [\alpha]_D + 177.4°$ (CHCl$_3$).

(E)-fluoromethylene-4-androsten-17-one 623 mg (E)-3-fluoromethylene-4-androsten-17-beta-ol is dissolved in 25 ml of toluene, mixed with 7 ml of cyclohexanone and three times with 300 mg of aluminum triisopropylate at 160° C. bath temperature on a water separator. After cooling, it is stirred with potassium sodium tartrate for 30 minutes at 60° C., diluted with dichloromethane, washed neutral, dried on sodium sulfate and concentrated. After chromatography on silica gel with hexane/ethyl acetate, 412 mg (E)-3-fluoromethylene-4-androsten-17-one with a melting point of 142°-143° C. is obtained.

$[\alpha]_D +235.8°$ (CHCl$_3$).

EXAMPLE 6

(Z)-3-fluoromethylene-4-androsten-17-one 1200 mg of (Z)-3-fluoromethylene-4-androsten-17-beta-ol is dissolved in 30 ml of acetone and mixed at 0° C. with 1.5 ml of Jones reagent. Then it is added to water, extracted three times with dichloromethane, washed neutral, dried on sodium sulfate and concentrated. After chromatography on silica gel with hexane/ethyl acetate, 842 mg of (Z)-3-fluoromethylene-4-androsten-17-one is obtained with a melting point of 101°-102° C.

$[\alpha]_D + 246.5°$ (CHCl$_3$).

EXAMPLE 7

3-Fluoromethylene-19-mercapto-4-androsten-17-one 17.2 g of fluoromethyl triphenylphosphonium tetrafluoroborate is suspended in 120 ml of tetrahydrofuran and mixed at 25° C. by portions with 7.8 g of potassium tert-butylate. Stirring is continued for one more hour, it is cooled to 0° C. and 1.5 g of 19-mercapto-4-androstene-3,17-dione (European patent 100,556) is instilled in 10 ml of tetrahydrofuran and stirring is continud for 30 more minutes. Then it is neutralized in 1N hydrochloric acid, the reaction mixture is added to waer, extracted 4 times with ethyl acetate, the organic phases washed neutral, dried on sodium sulfate and freed rom the solvent in a vacuum. After chromatography on silica gel with hexane/ethyl acetate, 752 mg of 3-fluoromethylene-19-mercapto-4-androsten-17-one with a melting point of 118°-120° C. is obtained.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A 3-methylene-4-androsten-17-one of formula I

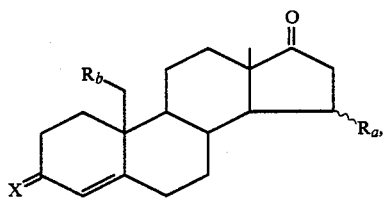

(I)

wherein $R_a$ is hydrogen; C$_{1-6}$-alkyl; C$_{1-6}$-alkenyl; C$_{1-6}$-alkyl or C$_{1-6}$-alkenyl substituted by hydroxyl, halo, C$_{1-4}$-alkanoyl, bis hydroxyl or bis C$_{1-4}$-alkanoyl, in which $R_a$ is in the alpha- or beta-position;

$R_b$ is hydrogen, hydroxyl or an —S(O)$_n$R$_c$ group, in which R$_c$ id hydrogen, C$_{1-4}$-alkyl or C$_{1-4}$-alkanoyl, n=0, 1 or 2, and X is CH$_2$, CHF, CHCl or CHBr, in which is R$_a$ is hydrogen and R$_b$ is hydroxyl, or R$_a$ and R$_b$ are each hydrogen, X is not CH$_2$.

2. A compound according to claim 1, wherein R$_a$ is methyl, ethyl, propyl, butyl, hexyl, 2-methylpropyl, 3-methylbutyl, ethenyl, hydroxylmethyl, 2-chloroethyl, 1-acetoxylethyl or 1,2-bis(acetoxy)butyl.

3. A compound according to claim 1, wherein R$_b$ is methylthio, ethylthio, propylsulfinyl, butylsulfonyl, or acetylthio.

4. A compound according to claim 1, which is 3-chloromethylene-19-methylthio-4-androsten-17-one,
   3-fluoromethylene-19-methylthio-4-androsten-17-one,
   15-alpha-ethyl-3-methylene-19-hydroxy-4-androsten-17-one,
   15-beta-ethyl-3-methylene-19-hydroxy-4-androsten-17-one,
   (E)-3-fluoromethylene-4-androsten-17-one,
   (Z)-3-fluoromethylene-4-androsten-17one, or
   3-fluoromethylene-19-mercapto-4-androsten-17-one.

5. A pharmaceutical composition comprising a compound of claim 1 and a pharmaceutically acceptable carrier.

6. A pharmaceutical composition comprising a compound of claim 4 and a pharmaceutically acceptable carrier.

7. A method of treating estrogen-stimulated tumors in a patient in need of such treatment, comprising administering an effective amount of a compound of claim 1 to said patient.

8. A method according to claim 7, wherein the effective amount of 0.001-100 mg/kg/day.

9. A method of ameliorating male infertility in a host comprising administering an effective amount of a compound of claim 1.

10. A method according to claim 9, wherein the effective amount is 0.001-100 mg/kg/day.

11. A method of inhibiting ovulation comprising administering to a female otherwise capable of ovulation an effective amount of a compound of claim 1.

12. A method according to claim 11, wherein the effective amount is 0.001-100 mg/kg/day.

13. A method of treating imminent myocardial infarction in a patient in need of such treatment, comprising administering an effective amount of a compound of claim 1.

14. A method according to claim 13, wherein the effective amount is 0.001-100 mg/kg/day.

15. A compound according to claim 1, wherein R$_a$ is in the β-position.

16. A compound according to claim 1, wherein R$_a$ is C$_{1-6}$-alkenyl or C$_{1-6}$-alkenyl substituted by hydroxyl, halo, C$_{1-4}$-alkanoyl, bis-hydroxyl or bis-C$_{1-4}$-alkanoyl.

17. A compound according to claim 1, wherein R$_b$ is —S(O)$_n$R$_c$, in which n is 1 or 2.

* * * * *